US006905824B2

(12) United States Patent
Rigby et al.

(10) Patent No.: US 6,905,824 B2
(45) Date of Patent: Jun. 14, 2005

(54) METHODS FOR DETERMINING ORGANISMS NOT REQUIRING THE SEPARATION OF FIXATIVE OR EXCESS PROBE

(75) Inventors: Susan Rigby, Acton, MA (US); Heather P. O'Keefe, Lexington, MA (US); Henrik Stender, Gentofte (DK)

(73) Assignee: Boston Probes, Inc., Bedford, MA (US)

( * ) Notice: Subject to any disclaimer, the term of this patent is extended or adjusted under 35 U.S.C. 154(b) by 9 days.

(21) Appl. No.: 10/017,445

(22) Filed: Dec. 14, 2001

(65) Prior Publication Data

US 2003/0165856 A1 Sep. 4, 2003

Related U.S. Application Data

(60) Provisional application No. 60/256,140, filed on Dec. 15, 2000.

(51) Int. Cl.[7] ........................... C12Q 1/68; C12P 19/34; C07H 21/02; C07H 21/04

(52) U.S. Cl. ........................ 435/6; 435/91.2; 536/23.5; 536/24.31; 536/24.33

(58) Field of Search ........................ 435/6, 91.1, 91.2; 536/23.1, 23.5, 24.31, 24

(56) References Cited

U.S. PATENT DOCUMENTS

| | | | | | |
|---|---|---|---|---|---|
| 5,225,326 | A | * | 7/1993 | Bresser et al. .................. | 435/6 |
| 5,527,675 | A | | 6/1996 | Coull et al. ..................... | 435/6 |
| 5,539,082 | A | | 7/1996 | Nielsen et al. ............... | 530/300 |
| 5,623,049 | A | | 4/1997 | Löbberding et al. ......... | 530/300 |
| 5,714,331 | A | | 2/1998 | Büchardt et al. .............. | 435/6 |
| 5,736,336 | A | | 4/1998 | Büchardt et al. .............. | 435/6 |
| 5,766,855 | A | | 6/1998 | Büchardt et al. .............. | 435/6 |
| 5,786,461 | A | | 7/1998 | Büchardt et al. .......... | 536/18.7 |
| 5,837,459 | A | | 11/1998 | Berg et al. ..................... | 435/6 |
| 5,891,625 | A | | 4/1999 | Büchardt et al. .............. | 435/6 |
| 5,972,610 | A | | 10/1999 | Büchardt et al. ............ | 530/350 |
| 5,986,053 | A | | 11/1999 | Ecker et al. ............... | 536/23.1 |
| 6,107,470 | A | | 8/2000 | Nielsen et al. ............. | 536/23.1 |
| 6,110,676 | A | | 8/2000 | Coull et al. ..................... | 435/6 |
| 6,150,097 | A | | 11/2000 | Tyagi et al. .................... | 435/6 |
| 6,403,309 | B1 | * | 6/2002 | Iris et al. ........................ | 435/6 |
| 2001/0010910 | A1 | * | 8/2001 | Hyldig-Nielsen et al. ...... | 435/6 |

FOREIGN PATENT DOCUMENTS

| | | |
|---|---|---|
| EP | 849363 | 6/1998 |
| WO | WO96/40709 | 12/1996 |
| WO | WO99/21881 | 5/1999 |
| WO | WO99/22018 | 5/1999 |
| WO | WO99/37670 | 7/1999 |
| WO | WO99/49293 | 9/1999 |

OTHER PUBLICATIONS

Braissant et al. Biochemica No. 1, 1998 pp. 10–16.*

Drobniewski et al. Journal of Clinical Microbiology vol. 38, No. 1, Jan. 2000, pp. 444–447.*

Ortiz et al. Molecular and Cellular Probes (1998) 12, 219–226.*

Yurov et al. Human Genetics (1996) 97: 390–398.*

Yurov, Y. et al, Application of cloned Satellite DNA Sequences to Molecular–Cytogenetic Analysis of Constitutive Heterochromatin Heteromorphisms in Man. Human Genetics, 76, 157–164 (1987).

Yurov, Y. et al, In Situ Hybridization of Cloned Repeating DNA Sequences and Differential Staining of Human Chromosomes. Laboratories of Genetics, All Union Mental Health Research Center, 97, 595–598 (1984).

Luk, J. et al, Rapid And Sensitive Detection Of Salmonella (0:6,7) By Immunomagnetic Monoclonal Antibody–Based Assays. Journal Of Immunological Methods, 1, 1–8 (1991).

Oliveira, K. et al. Differentiation of *Candida albicans* And *Candida Dubliniensis* By Fluorescent In Situ Hybridization With Peptide Nucleic Acid Probes. Journal Of Clinical Microbiology, 11, 4138–4141 (2001).

Perry O'Keefe, H. et al, Identification Of Indicator Microorganisms Using A Standardized PNA FISH Method. Journal of Microbiological Methods, 47, 281–292 (2001).

Pluskal, M. et al, Peptide Nucleic Acid Probes And Their Application In DNA and RNA Blot Hybridization Analysis. Journal Fed. Of American Soc. For Experimental Biology, 7, pA1264 (1994).

Stender, H. et al, A New Molecular Method for Simultaneous Identification And Enumeration Of Brettanomyces In Wine. American Society for Microbiology, 99, p. 516 (1999).

Stender, H. et al, Combination of ATP–Bioluminescence and PNA Probes Allow Rapid Total Counts And Identification Of Specific Microorganisms In Mixed Populations. Journal Of Microbiological Methods, 1, 69–75.

Stender, H. et al, Direct Detection And Identification Of *Mycobacterium tuberculosis* In Smear–Positive Sputum Samples By Fluorescence In Situ Hybridization (FISH) Using Peptide Nucleic Acid (PNA) Probes. Int. Tuberic Lung Dis. 9, 830–837 (1999).

*Primary Examiner*—Carla J. Myers
*Assistant Examiner*—Sally Sakelaris
(74) *Attorney, Agent, or Firm*—Brian D. Gildea

(57) ABSTRACT

This invention is directed to a rapid and simple method for determining organisms and/or cells in a sample. Generally, the method is directed to the use of molecular probes to selectively stain the organisms and/or cells for determination wherein growth medium, fixative reagents and/or excess molecular probes need not be separated before a determination is made.

21 Claims, 2 Drawing Sheets

OTHER PUBLICATIONS

Stender, H. et al, Fluorescence In Situ Hybridization Assay Using Peptide Nucleic Acid Probes For Differentiation Between Tuberculous And Nontuberculous *Mycobacterium* Species In Smears Of *Mycobacterium* Cultures. Journal of Clinical Microbiology. Applied and Environmental Microbiology, 2, 938–941 (2001).

Stender, H. et al, Identification of *Dekkera bruxellensis* (*Brettanomyces*) From Wine By Fluorescence In Situ Hybridization Using Peptide Nucleic Acid Probes. Applied And Environmental Microbiology, 2, 938–941 (2001).

Stender, H. et al, Rapid Detection, Identification, And Enumeration of *Escherichia coli* by Fluorescence In Situ Hybridization Using An Array Scanner. Journal Of Microbiological Methods, 1 (2001).

Stender, H. et al, Rapid Detection, Identification, And Enumeration Of *Pseudomonas* In Bottled Water Using Peptide Nucleic Acid Probes. Journal of Microbiological Methods, 3, 245–253 (2000).

Stender, H. et al, I–124. Simultaneous Identification And Enumeration of Microorganisms By Filter–Based In Situ Hybridixation Using Enzyme–Labeled Acid Probes. American Society For Microbiology, 100. p. 408 (2000).

Egholm, M. et al, PNA hybridizes to complementary oligonucleotides obeying the Watson–Crick hydrogenbonding rules. *Nature,* 365, 566–568 (1993).

O'Keefe, H. et al, Filter–based PNA *In Situ* hybridization for rapid detection, Identification and enumeration of specific micro–organisms. Journal of Applied Microbiology, 90, 180–189.

O'Keefe, H. et al, Identification of Indicator microorganisms using a standardized PNA FISH method. Journal Of Microbiological Methods, 47, 281–292 (2001).

O'Keefe, H. et al, Rapid detection, Identification, and enumeration of *Escherichia coli* by fluorescence In situ hybridization using an array scanner. Journal Of Microbiological Methods, 45, 31–39 (2001).

Yaron, A. et al, Intramolecularly Quenched Fluorogenic Substrates for Hydrolytic Enzymes. Analytical Biochemistry, 95, 228–235 (1979).

* cited by examiner

Figure 1    PNA FISH with Linear Beacon
A
B
Figure 2    PNA FISH with Flu labeled PNA Probe
A
B
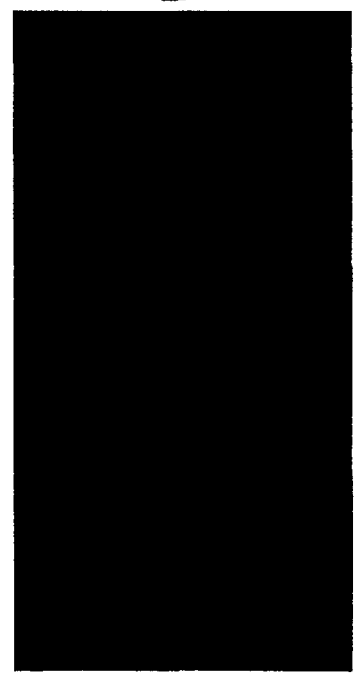

Figure 3 PNA FISH with Linear Beacon + Quencher PNA Probe
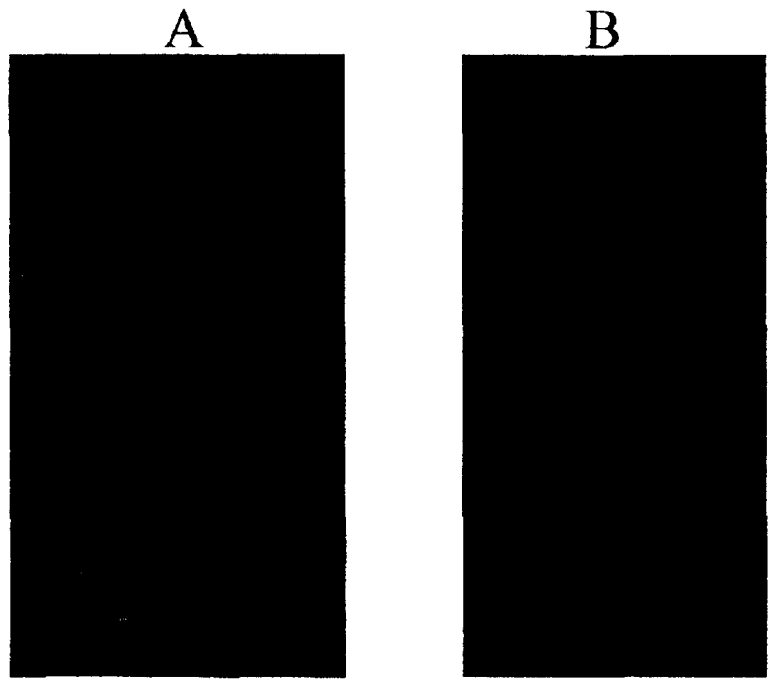
Figure 4 PNA FISH with Flu Labeled PNA Probe + Quencher PNA Probe
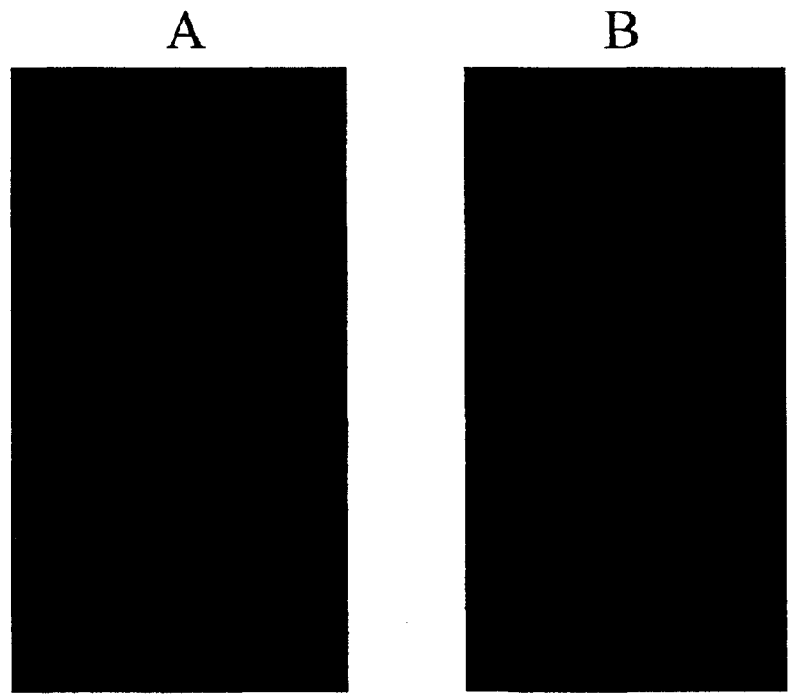

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probe Sequence
<220> FEATURE:
<221> NAME/KEY: misc_feature
<222> LOCATION: (1)
<223> OTHER INFORMATION: N-Terminal Flourescein Label with Linkers
<220> FEATURE:
<223> OTHER INFORMATION: Description of Artificial Sequence:PNA Probe
      Sequence

<400> SEQUENCE: 1
tcaatgagca aaggt                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probe Sequence
<220> FEATURE:
<221> NAME/KEY: misc_feature
<222> LOCATION: (1)
<223> OTHER INFORMATION: N-Terminal Flourescein With Linker
<220> FEATURE:
<221> NAME/KEY: misc_feature
<222> LOCATION: (15)
<223> OTHER INFORMATION: C-Terminal Dabcyl Label Linked Through a Lysine
      Moiety
<220> FEATURE:
<223> OTHER INFORMATION: Description of Artificial Sequence:PNA Probe
      Sequence

<400> SEQUENCE: 2
tcaatgagca aaggt                                                      15

<210> SEQ ID NO 3
<211> LENGTH: 8
<212> TYPE: DNA
<213> ORGANISM: Artificial Sequence
<220> FEATURE:
<223> OTHER INFORMATION: Description of Combined DNA/RNA Molecule:PNA
      Probe Sequence
<220> FEATURE:
<221> NAME/KEY: misc_feature
<222> LOCATION: (8)
<223> OTHER INFORMATION: C-Terminal Dabcyl Linked Through A Bis-Lysine
      Moiety
<220> FEATURE:
<223> OTHER INFORMATION: Description of Artificial Sequence:PNA Probe
      Sequence

<400> SEQUENCE: 3 ctcattga                                                               8

METHODS FOR DETERMINING ORGANISMS NOT REQUIRING THE SEPARATION OF FIXATIVE OR EXCESS PROBE

CROSS REFERENCE TO RELATED APPLICATIONS

This application claims the benefit of U.S. Provisional Application No. 60/256,140 filed on Dec. 15, 2000.

BACKGROUND OF THE INVENTION

1. Field of the Invention

This invention is related to the field of probe-based detection, analysis, identification and/or quantitation of organisms and/or cells.

2. Description of the Related Art

Nucleic acid hybridization is a fundamental process in molecular biology. Probe-based assays are useful in the detection, quantitation and/or analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, nucleic acid probe-based assays have been slow to achieve commercial success. This lack of commercial success is, at least partially, the result of difficulties associated with specificity, sensitivity and/or reliability.

Despite its name, Peptide Nucleic Acid (PNA) is neither a peptide, a nucleic acid nor is it an acid. Peptide Nucleic Acid (PNA) is a non-naturally occurring polyamide that can hybridize to nucleic acid (DNA and RNA) with sequence specificity (See: U.S. Pat. No. 5,539,082 and Egholm et al., *Nature* 365: 566–568 (1993)). Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization, which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature*, at p. 567). Because of their unique properties, it is clear that PNA is not the equivalent of a nucleic acid in either structure or function. Consequently, PNA probes need to be evaluated for performance and optimization to thereby confirm whether they can be used to specifically and reliably detect a particular nucleic acid target sequence, particularly when the target sequence exists in a complex sample such as a cell, tissue or organism.

A probe-based assay, whether performed using a nucleic acid or non-nucleic acid probe (e.g. a PNA), typically involves a multistep procedure wherein reagents are sequentially added to the sample containing the cells or organism and then removed by centrifugation (i.e. pelleting of the cells followed by a decanting of the reagents) and/or associated washing steps. In many cases, the organisms or cells of the sample are first grown in a medium to increase their total number and are then isolated from the growth medium before being treated with the assay reagents. At a minimum, the assay typically involves a step for the fixation of the cells or organisms and a step for the treatment of the cells or organisms with a molecular probe to thereby render the organisms or cells detectable. Applicants however, are not aware of any existing assay for the determination of cells or organisms that operates without separating the fixing reagent prior to the step of determination. Moreover, when cells are grown in a medium, Applicants are not aware of any assay for the determination of cells or organisms that operates without separating growth medium, fixing reagent and/or excess molecular probe prior to the step of determination.

SUMMARY OF THE INVENTION

In general, this invention is directed to a method for the analysis of organisms or cells. The method generally comprises first collecting a sample of organisms and/or cells to be analyzed. To the sample is then added one or more fixative agents to thereby fix the organisms or cells. The sample is also treated with one or more molecular probes, under suitable hybridization conditions, such that the organisms or cells react with the molecular probe in a way that produces organisms or cells that are detectably stained. Once the organisms or cells have been fixed and stained, they are then determined. For purposes of this invention, a determination means the act of determining the presence, absence, number, position and/or identity of a cell or organism in the sample. Nevertheless, it is an important advantage of the present invention that the fixative agent or agents and excess molecular probe or probes need not be separated from the organisms or cells prior to making the determination. Hence, this invention facilitates the rapid and simple determination of organisms and/or cells in a sample of interest.

BRIEF DESCRIPTION OF THE DRAWINGS

FIGS. 1–4, each with a Panel A & B, are prints of digital images taken with a microscope equipped with a CCD camera and a green filter. In each case Panel A represents the image taken when *E. coli* is the organism present in the sample and Panel B represents the image taken when *P. aeruginosa* is the organism present in the sample.

DETAILED DESCRIPTION OF THE INVENTION

1. Definitions

For the purposes of interpreting this specification the following definitions shall apply and whenever appropriate, terms used in the singular shall also include the plural and vice versa.

a. As used herein, a "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

b. As used herein, a "nucleobase sequence" means any segment of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), other nucleic acid mimics, nucleic acid analogs, and/or chimeras.

c. As used herein, a "target sequence" is the nucleobase sequence of a nucleic acid that is found in an organism or cell of interest and to which a molecular probe is designed to hybridize.

d. As used herein, a "nucleic acid" is a nucleobase sequence-containing polymer, or polymer segment, having a backbone formed from nucleotides, or analogs thereof.

e. As used herein, a "non-nucleic acid" is a nucleobase sequence containing polymer, or polymer segment, having a backbone formed from subunits that are not nucleotides, or analogs thereof. Peptide nucleic acids are a preferred non-nucleic acid polymer.

f. As used herein, the term "probe" or "molecular probe" means a nucleic acid or non-nucleic acid polymer (e.g. a DNA, RNA, PNA, nucleic acid analogs, nucleic acid mimics, chimera or linked polymer) having a probing nucleobase sequence that is designed to sequence specifically hybridize to a target sequence of an organism or cell of interest.

g. As used herein, a "detectable molecular probe" is a probe or molecular probe that is detectable by instrument or method.

h. As used herein, "stained" means that individual organisms and/or cells are directly or indirectly marked with a detectable moiety as a result of the sequence specific hybridization of one or more detectable molecular probes to a target sequence within the organism and/or cell.

i. As used herein, the term "peptide nucleic acid" or "PNA" means any oligomer, polymer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference. The term "peptide nucleic acid" or "PNA" shall also apply to polymers comprising two or more subunits of those nucleic acid mimics described in the following publications: Lagriffoul et al., *Bioorganic & Medicinal Chemistry Letters*, 4: 1081–1082 (1994); Petersen et al., *Bioorganic & Medicinal Chemistry Letters*, 6: 793–796 (1996); Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Diederichsen, U., *Bioorganic & Medicinal Chemistry Letters*, 7: 1743–1746 (1997); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Howarth et al., *J. Org. Chem.* 62: 5441–5450 (1997); Altmann, K-H et al., *Bioorganic & Medicinal Chemistry Letters*, 7: 1119–1122 (1997); Diederichsen, U., *Bioorganic & Med. Chem. Lett.*, 8: 165–168 (1998); Diederichsen et al., *Angew. Chem. Int. Ed.*, 37: 302–305 (1998); Cantin et al., *Tett. Lett.*, 38: 4211–4214 (1997); Ciapetti et al., *Tetrahedron*, 53: 1167–1176 (1997); Lagriffoule et al., *Chem. Eur. J.*, 3: 912–919 (1997); and the Peptide-Based Nucleic Acid Mimics (PENAMs) of Shah et al. as disclosed in WO96/04000.

In preferred embodiments, a PNA is a polymer comprising two or more subunits of the formula:

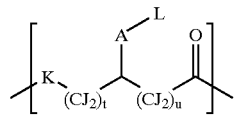

wherein, each J is the same or different and is selected from the group consisting of H, $R^1$, $OR^1$, $SR^1$, $NHR^1$, $NR_2^1$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; —$(CJ_2)_s$— and a group of the formula; —$(Cj_2)_sC(O)$—, wherein, J is defined above and each s is a whole number from one to five. Each t is 1 or 2 and each u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N—[2-(aminoethyl)] glycine backbone through a methylene carbonyl linkage.

j. As used herein, the terms "label" and "detectable moiety" are interchangeable and refer to moieties that can be attached to a molecular probe to thereby render the molecular probe detectable by an instrument or method.

k. As used herein, the term "chimera" or "chimeric oligomer" means a polymer comprising two or more linked subunits that are selected from different classes of subunits. For example, a FNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally and non-naturally occurring amino acid subunits, DNA subunits, RNA subunits and subunits of analogues or mimics of nucleic acids.

l. As used herein, the term "linked polymer" means a polymer comprising two or more polymer segments that are linked by a linker. The polymer segments that are linked to form the linked polymer are selected from the group consisting of an oligodeoxynucleotide (DNA), an oligoribonucleotide (RNA), a peptide, a polyamide, a peptide nucleic acid (PNA) and a chimera.

2. Description of the Invention

I. General

Nucleic Acid Synthesis and Modification

Nucleic acid oligomer (oligonucleotide and oligoribonucleotide) synthesis has become routine. For a detailed description of nucleic acid synthesis please see Gait, M. J., *Oligonucleotide Synthesis: a Practical Approach*, IRL Press, Oxford England. Those of ordinary skill in the art will recognize that both labeled or unlabeled oligonucleotides (DNA, RNA and synthetic analogues thereof) are readily available. They can be synthesized using commercially available instrumentation and reagents or they can be purchased from commercial vendors of custom manufactured oligonucleotides. Patents that discuss various compositions, supports and methodologies for the synthesis and labeling of nucleic acids include: U.S. Pat. Nos. 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198,540, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732; all of which are herein incorporated by reference.

PNA Synthesis

Methods for the chemical assembly of PNAs are well known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference (Also see: PerSeptive Biosystems Product Literature)). As a general reference for PNA synthesis methodology also please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling

Preferred non-limiting methods for labeling PNAs are described in U.S. Pat. No. 6,110,676, WO99/22018, WO99/21881, WO99/37670 and WO99/49293, the examples section of this specification or are otherwise well known in the art of PNA synthesis and peptide synthesis. Methods for labeling PNA are also discussed in Nielsen et al., *Peptide Nucleic Acids; Protocols and Applications*, Horizon Scientific Press, Norfolk England (1999).

Labels & Labeled Probes

The molecular probes that are used for the practice of this invention are labeled with a detectable moiety. By operation of the method, the labeled probe or probes hybridize to a target sequence within an organism or cell of interest and thereby detectably stain the organism or cell. The staining process may be direct, such as with a fluorescently labeled molecular probe, or may be indirect, such as with an enzyme labeled probe wherein the stain is generated by operation of the enzyme acting or a substrate that is present.

Non-limiting examples of detectable moieties (labels) suitable for directly labeling molecular probes used in the practice of this invention include a dextran conjugate, a branched nucleic acid detection system, a chromophore, a fluorophore, a spin label, a radioisotope, an enzyme, a hapten, an acridinium ester and a chemiluminescent compound. Other suitable labeling reagents and preferred methods of attachment would be recognized by those of ordinary skill in the art of PNA, peptide or nucleic acid synthesis.

Preferred haptens include 5(6)-carboxyfluorescein, 2,4-dinitrophenyl, digoxigenin, and biotin.

Preferred fluorochromes (fluorophores) include 5(6)-carboxyfluorescein (Flu), 6-((7-amino-4-methylcoumarin-3-acetyl)amino)hexanoic acid (Cou),5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), JOE, Tamara or the Alexa dye series (Molecular Probes, Eugene, Oreg.).

Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP)).

Self-Indicating Probes

In another embodiment, the probes used in the method of this invention are self-indicating probes. Generally, the labels attached to self-indicating probes. Generally, the labels attached to self-indicating probes comprise a set (hereinafter "Beacon Set(s)") of energy transfer moieties comprising at least one energy transfer donor and at least one energy transfer acceptor moiety. Typically, the Beacon Set will include a single donor moiety and a single acceptor moiety. Nevertheless, a Beacon Set may contain more than one donor moiety and/or more than one acceptor moiety. The donor and acceptor moieties operate such that one or more acceptor moieties accepts energy transferred from the one or more donor moieties or otherwise quenches the signal from the donor moiety or moieties. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo) benzoic acid (dabcyl).

Transfer of energy between donor and acceptor moieties of a self-indicating probe may occur through collision of the closely associated moieties of a Beacon Set(s) or through a non radiative process such as fluorescence resonance energy transfer (FRET). For FRET to occur, transfer of energy between donor and acceptor moieties of a Beacon Set requires that the moieties be close in space and that the emission spectrum of a donor(s) have substantial overlap with the absorption spectrum of the acceptor(s) (See: Yaron et al. *Analytical Biochemistry*, 95: 228–235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228–235 (1979) and particularly page 229, col. 1 through page 232, col. 1). This process is referred to as intramolecular collision since it is believed that quenching is caused by the direct contact of the donor and acceptor moieties (See: Yaron et al.). The following is offered as a non-limiting list of examples of this type of self-indicating probe:

(i) Linear Beacons

In a preferred embodiment, the self-indicating probe is a Linear Beacon as more fully described in co-pending and commonly owned patent application U.S. Ser. No. 09/179, 162, entitled: "Methods, Kits And Compositions Pertaining To Linear Beacons", herein incorporated by reference. The related PCT application has also now published as WO99/21881.

(ii) PNA Molecular Beacons

In another preferred embodiment, the self-indicating probe is a PNA Molecular Beacon as more fully described in co-pending patent application: U.S. Ser. No. 09/179,298 (now allowed), entitled: "Methods, Kits And Compositions Pertaining To PNA Molecular Beacons", herein incorporated by reference. The related PCT application has also now published as WO99/22018.

(iii) DNA Molecular Beacons

In a preferred embodiment, the self-indicating probe is a nucleic acid molecular beacon as more fully described in U.S. Pat. No. 5,925,517, entitled: "Detectably Labeled Dual Conformation Oligonucleotide Probes, Assays and Kits", herein incorporated by reference. Reference is also made to recently published: U.S. Pat. No. 6,150,097, entitled: "Nucleic Acid Detection Probes Having Non-Fret Fluorescence Quenching And Kits And Assays Including Such Probes".

(iv) Detection Complexes

In a preferred embodiment, the self-indicating probe is a Detection Complex as more fully described co-pending patent application: U.S. Ser. No. 09/275,848 (now allowed), entitled: "Methods, Kits And Compositions Pertaining To Detection Complexes", herein incorporated by reference. The related PCT application has also now published as WO99/49293.

Detecting Energy Transfer

Hybrid formation of a self-indicating probe with a target sequence can be monitored by measuring at least one physical property of at least one member of the Beacon Set that is detectably different when the hybridization complex is formed as compared with when the "Beacon" probe exists in the absence of target sequence. We refer to this phenomenon as the self-indicating property of the probes. This change in detectable signal results from the change in efficiency of energy transfer between the donor and acceptor caused by hybridization of the molecular probe to the target sequence. Preferably, the means of detection will involve measuring fluorescence of a donor or acceptor fluorophore of a Beacon Set. Most preferably, the Beacon Set will comprise at least one donor fluorophore and at least one acceptor quencher such that the fluorescence of the donor fluorophore is used to detect, identify or quantitate hybridization of the probe to the target sequence.

Other Self-Indicating Probes

In another embodiment, the self-indicating probe or probes used in this invention are of the type described in WIPO patent application WO97/45539, herein referred to as an "intercalating beacon". These intercalating beacons incorporate a reporter group that interacts with the nucleic acid to thereby produce a detectable signal. Preferably, the probes of WO97/45539, as used in this invention, are appropriately labeled peptide nucleic acids that produce detectable signal upon hybridization to the target sequence.

Detectable and Independently Detectable Moieties/Multiplex Analysis

In preferred embodiments of this invention, a multiplex hybridization assay is performed. In a multiplex assay, numerous conditions of interest are simultaneously or sequentially examined. Multiplex analysis relies on the ability to sort sample components or the data associated therewith, during or after the assay is completed. In preferred embodiments of the invention, one or more distinct independently detectable moieties are used to label two or more different molecular probes used in an assay. The ability to differentiate between and/or quantitate each of the independently detectable moieties provides the means to multiplex a hybridization assay because the data that correlates with the hybridization of each of the distinct, independently labeled molecular probe to a particular target sequence within an organism or cell of interest can be correlated with the presence, absence, number, position or identity of that organism and/or cell sought to be detected in the sample. Consequently, the multiplex assays of this invention may be used to simultaneously or sequentially detect the presence, absence, number, position or identity of two or more organisms and/or cells in the same sample and in the same assay.

Spacer/Linker Moieties

Generally, spacers are used to minimize the adverse effects that bulky labeling reagents might have on hybridization properties of probes. Linkers typically induce flexibility and randomness into the probe or otherwise link two or more nucleobase sequences of a molecular probe. Preferred spacer/linker moieties for the nucleobase polymers used in this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the molecular probe (For example see: Gildea et al., *Tett. Lett.* 39: 7255–7258 (1998)). Preferably, a spacer/linker moiety comprises one or more linked compounds having the formula: —Y—$(O_m)$—$(CW_2)_n)_o$—Z—. The group Y is selected from the group consisting of: a single bond, —$(CW_2)_p$—, —C(O)$(CW_2)_p$—, —C(S)$(CW_2)_p$— and —S($O_2$)$(CW_2)_p$. The group Z has the formula NH, $NR^2$, S or O. Each W is independently H, $R^2$, —$OR^2$, F, Cl, Br or I; wherein, each $R^2$ is independently selected from the group consisting of: —$CX_3$, —$CX_2CX_3$, —$CX_2CX_2CX_3$, —$CX_2CX(CX_3)_2$, and —$C(CX_3)_3$. Each X is independently H, F, Cl, Br or I. Each m is independently 0 or 1. Each n, o and p are independently integers from 0 to 10.

Hybridization Conditions/Stringency

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a molecular probe/target sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Nevertheless, aided by no more than routine experimentation and the disclosure provided herein, those of skill in the art will easily be able to determine suitable hybridization conditions for performing assays utilizing the methods and compositions described herein.

Blocking Probes

Blocking probes are nucleic acid or non-nucleic acid probes that can be used to suppress the binding of the probing nucleobase sequence of the probing polymer to a non-target sequence. Preferred blocking probes are PNA probes (See: Coull et al., U.S. Pat. No. 6,110,676, herein incorporated by reference). Typically, blocking probes are closely related to the probing nucleobase sequence and preferably they comprise one or more single point mutations as compared with the probe sought to be detected in the assay. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods and compositions of this invention to suppress the binding of the nucleic acid or non-nucleic acid molecular probe to a non-target sequence that might be present in the organism to be distinguished and otherwise interfere with the performance of the assay.

Probing Nucleobase Sequence

The probing nucleobase sequence of a molecular probe is the specific sequence recognition portion of the construct. Therefore, the probing nucleobase sequence is a nucleobase sequence designed to hybridize to a specific target sequence of the cells or organisms of interest in a sample. Consequently, with due consideration to the requirements of a molecular probe for the assay format chosen, the length and sequence composition of the probing nucleobase sequence of the molecular probe will generally be chosen such that a stable complex is formed with the target sequence under suitable hybridization.

Probe Complexes

In still another embodiment, two probes are designed to, in the aggregate, produce a probing nucleobase sequence that hybridizes to the target sequence sought to be detected and thereby generates a detectable signal whereby the nucleobase sequence of each individual molecular probe comprises half or approximately half of the complete complement to the target sequence. As a non-limiting example, the nucleobase sequences of the two probes might be designed using the assay as described in European Patent Application 849,363, entitled: "Method of identifying a nucleic acid using triple helix formation of adjacently annealed probes" by H. Orum et al. (See: EPA 849,363). Similar compositions comprising a PNA probe triplex have been described in commonly owned U.S. Pat. No 6,287,772. Using this methodology, the probes that hybridize to the target sequence may or may not be labeled since it is the probe complex formed by the annealing of the adjacent probes that is directly detected and not the probes that directly bind to the target sequence.

Advantages Of The Present Invention

It is an advantage of the present invention that washing and/or separation steps of the overall assay can be eliminated thereby reducing the total work and time required to perform the method. For example, the analysis of organisms, such as *E. coli* or Salmonella, that have been grown in culture can be done in a little over one hour. This allotted time includes all the time required for performing the assay; including removing a sample from the culture for analysis and performing the assay until the result is reported. The ability to perform the determination in such a rapid manner is facilitated by the novel assay described herein wherein all steps involving separation/washing have been omitted. Applicants are unaware of any comparable assay that is so easy and fast as the assay described herein.

II. Preferred Embodiments of the Invention

In one embodiment, this invention is directed to a method for the analysis of organisms and/or cells. The method generally comprises first collecting a sample of organisms and/or cells to be analyzed provided however that, as used herein, the act of collecting is not intended to prohibit, and may in fact involve, a preconditioning of the sample to remove extraneous materials that might interfere with the assay. To the sample, as collected, is then added one or more fixative agents to thereby fix the organisms or cells. The sample is also treated with one or more molecular probes, under suitable hybridization conditions, such that the organisms and/or cells react with the molecular probe or probes in a way that produces organisms and/or cells that are detectably stained with detectable or independently detectable moieties. Once the organisms and/or cells have been fixed and stained, they are then determined. For purposes of this invention, a determination means the act of determining the presence, absence, number, position and/or identity of a cell or organism in the sample.

Nevertheless, it is an important advantage of the present invention that the fixative agent or agents and excess molecular probe or probes are not separated from the organisms or cells prior to making the determination. Hence, the method facilitates a rapid and simple way to determine organisms or cells in a sample of interest.

According to the method, either nucleic acid or non-nucleic acid probes may be used. However, the use of PNA probes, as the molecular probe, is preferred because the assay can then be performed more rapidly and with greater sensitivity and reliability.

According to the method, it is not important whether organisms or cells are determined. Moreover, when performing multiplex assays, it my be possible, or even preferable to detect both a cell or cells or interest as well as an organism or organisms of interest in the same sample and in the same assay. Nothing described herein is intended to be limiting in this regard.

According to the method, the organisms and/or cells to be analyzed can be either collected from a growth medium used increase the total number of organisms or cells available for analysis or, when the cells or organisms are sufficiently abundant in the sample, they can be collected directly from a sample without being treated for growth. It is an additional advantage of this invention that, when growth medium is used, the growth medium need not be completely separated from the organisms or cells of the sample. As used herein growth medium includes both broth and agar. According to the method, the growth medium may in certain cases be reduced in volume, such as by pelleting the organisms and/or cells and then removing a portion of the medium, but need not be completely removed. Again, this has the advantage of saving time and labor expended in performing the assay.

When performing the assay, Applicants have observed that the addition of a conventional blocking reagent, such as casein, substantially improves the performance of the assay when it is present during hybridization of the molecular probe. Without intending to be bound to this theory, it is believed that the blocking reagent inhibits the reaction of the molecular probe with components of the fixative, and growth medium if present, and thereby bolsters the interaction of the molecular probe with the target sequence.

According to the method, there is no requirement that the organisms and/or cells be fixed before hybridization. It is possible to either fix the cells or organisms before treatment with the molecular probe or else simultaneously fix the cells or organisms while treating the sample with the molecular probe or probes.

According to the method, one or more labeled molecular probes is used to stain the organisms or cells, if present in the assay. Preferably, the molecular probe or probes are labeled with one or more fluorophores. In certain preferred embodiments, two or more independently detectable molecular probes are used in the method for the multiplex analysis of two or more different types of organisms and/or cells. It is noted that the number of different organisms or cells that can be analyzed in a single multiplex assay is limited only by the number of different independently detectable molecular probes that can be produced. In a preferred embodiment, the two or more independently detectable molecular probes are labeled with independently detectable fluorophores.

As previously discussed, the molecular probes may be of the self-indicating type. By self-indicating, we mean that there is a change that occurs in detectable signal of at least label attached to one the probe when it hybridizes to the target sequence inside the organism of cell. As discussed above, a non-limiting list of self-indicating molecular probes includes: a linear beacon, a nucleic acid or PNA molecular beacon and an intercalating beacon.

An alternative embodiment of a self-indicating probe is a detection complex. A detection complex differs from the aforementioned constructs in that it comprises a complex of at least two polymers wherein the labels that comprise the Beacon Set are split between two polymers of the complex such that they interact when the complex is formed but do not interact if the complex becomes dissociated (See: WO99/49293). Hence, for this embodiment, the Detection Complex, that is the molecular probe, is added to the assay. The complex will dissociate to generate a detectable change in signal whenever one of the component polymers of the complex hybridizes to the target sequence inside the organism or cell.

In still another embodiment of the method, it is possible to, after fixation and treatment with the molecular probe has been performed, add a quencher labeled oligomer to the assay before the determination is made, wherein the quencher moiety of the oligomer quenches signal from the label of the molecular probe if it hybridizes to the molecular probe. In this way a complex between the excess molecular probe and the quencher labeled oligomer is formed and thereby quenches the signal from the excess molecular probe. Because signal from the excess probe is quenched, the excess molecular probe does not generate a large background. It is noted that because the labeled probe or probes are hybridized to the target sequence within the organism or cell, the quencher labeled oligomer cannot hybridize to these signal generating probes to thereby suppress the detectable signal.

According to the method, the cells or organisms can be determined in any manner that allows for the observation and analysis of the stained organisms and/or cells. In preferred embodiments, the cells and/or organisms of the sample are determined using either a microscope, array scanner or a flow cytometer.

EXAMPLES

This invention is now illustrated by the following examples that are not intended to be limiting in any way.

Example 1

PNA Oligomers as Molecular Probes

PNA Oligomers were prepared from commercial reagents and instrumentation obtained from Applied Biosystems, Foster City, Calif. using well known methods and those disclosed in published PCT applications WO99/21881, WO99/22018 and WO99/49293.

PNA Oligomers Prepared

TABLE 1

| Probe ID | PNA Probe Sequence | Seq. ID No. |
|---|---|---|
| Flu Labeled PNA Probe | Flu-OEE-TCA-ATG-AGC-AAA-GGT-EE-NH$_2$ | 1 |
| PNA Linear Beacon | Flu-O-TCA-ATG-AGC-AAA-GGT-Lys(dabcyl)—NH$_2$ | 2 |
| Quencher PNA Oligomer | H-CTC-ATT-GA-Lys-Lys(dabcyl)—NH$_2$ | 3 |

All PNA sequences are written from the amine (N—) terminus to the carboxyl (C—) terminus. Flu=5(6)-carboxyfluorescein; O=8-amino-3,6-dioxaoctanoic acid; dabcyl=4-((4-(dimethylamino)phenyl)azo)benzoic acid; Lys=the amino acid L-lysine; and E is shown below (See: U.S. Pat. No. 6,326,479).

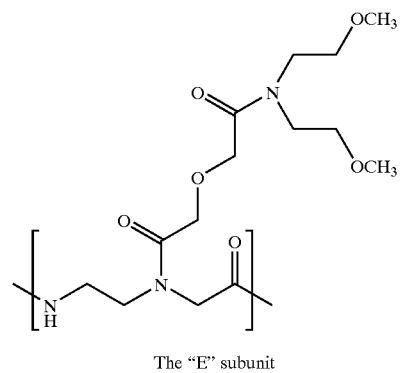

The "E" subunit

Experimental Methods

Assay Design

A rapid, simple PNA FISH assay for detection of *E. coli* was developed. The method involves fixation of bacteria directly from culture, followed by hybridization with an *E. coli* specific PNA probe. The example described below demonstrate that this protocol can be used with a standard Flu (fluorescein) Labeled PNA Probe as well as a self-indicating fluorescein labeled PNA Linear Beacon. Additionally we have shown that the use of a Quencher Labeled PNA Probe, that is complementary to the *E. coli* specific PNA probes (both the Flu labeled PNA probe and the PNA Linear Beacon) and contains a dabcyl at the carboxyl terminus, is effective for the reduction of background.

Fixation of Cells

A sample of 1 mL of an exponentially growing culture of both *E. coli* (8739) or *P. aeruginosa* (27853), obtained from the American Type Culture Collection, Manassas, Va., was pelleted by centrifugation at 10,000 rpm for 5 minutes. Approximately 700 μL of medium was removed from each sample and the cell pellets were then resuspended in the remaining medium (approximately 300 μL). To 6 μL of the resulting cell suspension, that had been transferred to a separate tube, was added 4 μL of Buffer B. The fixation reaction was then incubated for 15 minutes at room temperature.

Buffer Solutions

| | |
|---|---|
| A | 130 mM NaCl, 7 mM Na₂HPO₄, 7 mM NaH₂PO₄, pH 7.0 |
| B | 10% (w/v) paraformaldehyde in Buffer A |
| C | 25 mM Tris pH 9.0, 0.5% SDS (w/v), 100 mM NaCl, 1% casein (w/v) |

Hybridization and Visualization

For hybridization, 110 µL of Buffer C was added directly to the 10 µL fixation reaction. For each sample of either *E. coli* or *P. aeruginosa* was added one of either the Flu Labeled PNA Probe or the PNA Linear Beacon at a final concentration of 120 nM. Reactions were incubated at 55° C. for 30 minutes. For experiments in which the Quencher PNA Oligomer was also used, this oligomer was, at a concentration of 960 nM, added after the hybridization step was completed; followed by a 30 minute incubation at 55° C. All reactions were analyzed by spreading 2 µL of the incubated sample on a preheated microscope slide (~60° C.). The slide was then dried on a heat block set at approximately 60° C. To each slide was then added 2 µL of mounting media (Vector Laboratories) and a coverslip was applied. The reactions were examined microscopically using a 60× objective and a FITC filter.

Results

FIGS. 1–4, each with a Panel A & B, are prints of digital images taken with a microscope equipped with a CCD camera and a green filter. In each case Panel A represents the image taken when *E. coli* is the organism present in the sample and Panel B represents the image taken when *P. aeruginosa* is the organism present in the sample. In all cases, the *E. coli* in Panel A can be easily detected without regard to the protocol or probe type. This is the expected result since in all cases, the probe is specific for detecting *E. coli*. By comparison, the *P. aeruginosa* is not very equally detectable in Panel B of the Figures, without regard to the protocol or probe type. This also is the expected result since there is not expected to be a sequence complementary to the probe in the nucleic acid of *P. aeruginosa*.

With reference to FIG. 1, it is clear that the PNA Linear Beacon can be used to produce a positive result for the organism sought to be detected, *E. coli* (Panel A), while the negative result in Panel B demonstrates that the *P. aeruginosa* bacteria can be discriminated. In this case, the excess self-reporting PNA Linear Beacon is not expected to give rise to a substantial background fluorescence since it is self-quenching.

With reference to FIG. 2, it is clear that the Flu Labeled PNA Probe can be used to produce a positive result for the organism sought to be detected, *E. coli* (Panel A), while the negative result in Panel B demonstrates that the *P. aeruginosa* bacteria can be discriminated. In this case, it is somewhat surprising that the excess PNA probe, although not considered to be a self-indicating probe, does not give rise to a substantial background fluorescence.

The data shown in FIGS. 3 and 4 were generated using protocols that are identical to those used to generate FIGS. 1 and 2, respectively, except that the Quencher PNA Oligomer was also added as described above. With reference to FIGS. 3 & 4, it is clear that the presence of the Quencher PNA Oligomer does not produce a substantially different result. More specifically, it is clear that regardless of the probe type used, a positive result is obtained for the organism sought to be detected, *E. coli* (Panel A), while the assay is still able to discriminate the *P. aeruginosa* bacteria (Panel B). However, it is clear by comparing FIG. 2, Panel A with FIG. 4, Panel A, that the presence of the Quencher PNA Oligomer reduce the overall background "haze", likely due to the excess Flu Labeled PNA Oligomer, but also appears to slightly reduce detectable signal. By comparison, a review of FIG. 1, Panel A and FIG. 3, Panel A, indicates that the Quencher PNA Oligomer also appears to reduce the overall background "haze", likely due to the excess PNA Linear Beacon, but does not appear to reduce detectable signal.

Most advantageously this PNA FISH protocol eliminates the need for time consuming wash and centrifugation steps, thereby allowing for reliable detection of *E. coli* in 1–1.5 hours depending on whether or not the Quencher PNA Oligomer is used.

Example 2

Multiple Species Examination

TABLE 2

| Species | Strain ID | Result |
|---|---|---|
| *Escherichia coli* | ATCC 8739 | + |
| *Escherichia coli* | ATCC 25922 | + |
| *Escherichia coli* | ATCC 8739 | + |
| *Escherichia coli* | Isolate | + |
| *Escherichia coli* | Isolate | + |
| *Escherichia coli* | Isolate | + |
| *Pseudomonas aeruginosa* | ATCC 27853 | – |
| *Bacillus subtilis* | ATCC 6633 | – |
| *Pseudomonas putida* | ATCC 12633 | – |
| *Staphylococcus aureus* | ATCC 6538 | – |
| *Listeria monocytogenes* | ATCC 7644 | – |
| *Shigella sonnei* | ATCC 29930 | + |
| *Shigella flexneri* | ATCC 29903 | + |
| *Salmonella choleraesuis* | ATCC 29946 | – |
| *Micrococcus luteus* | ATCC 9341 | – |
| *Yersinia enterocolitica* | Isolate | – |
| *Proteus mirabilis* | ATCC 12453 | – |
| *Citrobacter freundii* | ATCC 8090 | – |
| *Enterococcus aerogenes* | ATCC 49701 | – |
| *Klebsiella pneumoniae* | Isolate | – |
| *Acinotobacter calcoaceticus* | ATCC 23055 | – |

+: Strong fluorescent signal.
–: Weak fluorescent signal clearly distinguishable from the signal obtained with *E. coli*.

In view of the positive results described above, more extensive experimentation was performed wherein numerous species of organism were examined in the same manner, except in this case images are not provide but the intensity of the cells was visually observed and then scored. The results are summarized in the Table 2, below. The probe used in this Example was the Linear PNA Beacon described above.

With reference to Table 2, it is clear that the Linear PNA Beacon, that was reasonably specific for *E. coli*, hybridizes with the various *E. coli* strains and does not react with other organisms, except for species of *Shigella*. However, it is well known in the art that distinction between *E. coli* and *Shigella* is quite difficult since the rRNA is almost identical. In this case the Linear PNA Beacon is completely complementary to the rRNA of *Shigella*. Accordingly, it is expected that the Linear PNA Probe with this particular nucleobase sequence will hybridize as completely with the *Shigella* as it does with the rRNA of *E. coli*. Thus, the results are as they should be expected in view of the nature of the Linear FNA Beacon probe used.

We claim:

1. A method for the analysis of organisms, cells or both organisms and cells; said method comprising:

a) collecting a sample of organisms or cells;

b) adding one or more fixative agents to the sample to thereby fix the organisms, cells or both;

c) treating the sample with one or more molecular probes, under suitable hybridization conditions, such that the organisms, cells or both react with the molecular probe in a way that produces detectable or independently detectable organisms, cells or both; and d) determining one or more of the detectable organisms or cells in the sample; wherein the method does not include one or more washing steps to remove the fixative agent or agents and the excess molecular probe or probes from the organisms or cells prior to making the determination.

2. The method of claim 1, wherein the organisms, cells or both are collected from a growth medium.

3. The method of claim 1, wherein the organisms, cells or both are collected directly from a sample that has not been treated with a growth medium.

4. The method of claim 2, wherein the growth medium is not completely separated from the sample of organisms, cells or both.

5. The method of claim 2, wherein the growth medium is selected from the group consisting of broth and agar.

6. The method of claim 1, wherein a blocking agent is present during the operation of step (c).

7. The method of claim 6, wherein the blocking agent is casein.

8. The method of claim 1, wherein steps (b) and (c) are performed simultaneously.

9. The method of claim 1, wherein steps (b) and (c) are performed sequentially in that order.

10. The method of claim 1, wherein the molecular probe is labeled with a fluorophore.

11. The method of claim 1, wherein two or more independently detectable molecular probes are used in the method for the multiplex analysis of two or more different types of organisms or cells in the sample.

12. The method of claim 11, wherein the two or more independently detectable molecular probes are labeled with independently detectable fluorophores.

13. The method of claim 1, wherein the molecular probe is a self-indicating molecular probe selected from the group consisting of a linear beacon, a nucleic acid or PNA molecular beacon and an intercalating beacon.

14. The method of claim 1, wherein the molecular probe is a detection complex.

15. The method of claim 1, further comprising:
e) adding a quencher labeled oligomer before the determination is made to thereby form a complex between the excess molecular probe and the quencher labeled oligomer.

16. The method of claim 1, wherein the cells or organisms of the sample are determined using either a microscope, an array scanner or a flow cytometer.

17. The method of claim 1, wherein one or more blocking probes are present during the operation of step (c).

18. The method of claim 1, wherein the molecular probe is a nucleic acid probe.

19. The method of claim 1, wherein the molecular probe is a non-nucleic acid probe.

20. The method of claim 19, wherein the non-nucleic acid probe is a peptide nucleic acid probe.

21. The method of claim 1, wherein the method is for determining organisms, cells or both, said method comprising:

a) treating a sample of fixed cells, organisms or both, that have been grown in a medium, with one or more detectable molecular probes, under suitable hybridization conditions, in a way that produces stained organisms, cells or both stained organisms and cells; and b) determining the stained cells, organism or both the stained organisms and cells;

wherein the medium is not removed or separated from the organisms, cells or both the organisms and cells.

* * * * *